(12) United States Patent
Arbogast

(10) Patent No.: US 6,642,055 B1
(45) Date of Patent: Nov. 4, 2003

(54) METHOD FOR THE PREDICTION OF PREECLAMPSIA AND OTHER DISEASES

(75) Inventor: Bradley W. Arbogast, Johnson City, TN (US)

(73) Assignee: Arbogast Pharmaceuticals, Inc., Johnson City, TN (US)

( * ) Notice: Subject to any disclaimer, the term of this patent is extended or adjusted under 35 U.S.C. 154(b) by 0 days.

(21) Appl. No.: 09/540,809

(22) Filed: Mar. 31, 2000

(51) Int. Cl.$^7$ .............................................. G01N 33/00
(52) U.S. Cl. .............................. 436/88; 436/16; 436/71
(58) Field of Search ............................... 436/16, 71, 88

(56) References Cited

U.S. PATENT DOCUMENTS

| | | |
|---|---|---|
| 4,349,625 A | 9/1982 | Okada |
| 4,699,878 A | 10/1987 | Arbogast |
| 5,079,171 A | 1/1992 | Senyei |
| 5,094,943 A | 3/1992 | Siedel et al. |
| 5,108,898 A | 4/1992 | Peters |
| 5,198,366 A | 3/1993 | Silberman |
| 5,238,819 A | 8/1993 | Roberts |
| 5,534,548 A | 7/1996 | Killian |
| 5,543,138 A | 8/1996 | Keith |
| 5,580,554 A | 12/1996 | Keith |
| 5,712,103 A | 1/1998 | Leavitt |
| 5,811,416 A | 9/1998 | Chwalisz |
| 5,849,474 A | 12/1998 | Olson |

FOREIGN PATENT DOCUMENTS

| | | |
|---|---|---|
| WO | WO 90/00365 | 1/1990 |

OTHER PUBLICATIONS

Arbogast, BW, et al. Which Plasma Factors Bring about Disturbance of Endothelial Function in Preeclampsia? The Lancet. vol. 343 (1994) 340–341.

Arbogast, BW, et al. Coronary Disease Prediction Using a New Atherogenic Index. Atherosclerosis, Vol 66 (1987) 555–62.

(List continued on next page.)

Primary Examiner—Jill Warden
Assistant Examiner—Monique T. Cole
(74) Attorney, Agent, or Firm—Susan F. Johnston

(57) ABSTRACT

The invention disclosed is a process for determining the cytoprotective activity of plasma that prevents the destruction of endothelial cells and forestalls the development of a number of diseases such as atherosclerosis, preeclampsia, edema, nephrotic syndrome, and stroke. The present invention includes a method of diagnosing a patient's proclivity to develop a disease having a correlation to a reduction in the concentration of pI 5.6 albumin in the plasma by determining a value indicative of the concentration of the pI 5.6 albumin that is not bound to VLDL ("free pI 5.6 albumin") in the patient's blood serum. The preferred embodiment of the process utilizes in vitro methods to obtain an indicator of the free pI 5.6 albumin instead of directly measuring the concentration of the free pI 5.6 albumin. The preferred method comprises the steps of:

(a) providing a plasma sample containing free albumin, triglycerides, very low density lipoproteins, low density lipoproteins, and non-esterified fatty acids bound to the free albumin;

(b) determining the concentration of the free albumin;

(c) determining the concentration of the non-esterified fatty acids bound to the free albumin; and (d) calculating a value indicative of the toxicity preventing ability of the plasma by comparing the concentration of the free albumin to the concentration of the non-esterified fatty acids bound to the free albumin. The present process does not provide direct measurement of the cytoprotective activity of plasma, but rather, an empirical value which has clinical relevance in identifying patients with a high chance of developing diseases inhibited by pI 5.6 albumin.

15 Claims, 5 Drawing Sheets

OTHER PUBLICATIONS

Chi, D.S., et al. Inhibition of In Vitro Lymphocyte Response by Streptozotocin–Induced Diabetic Rat Serum: A Function of Very–Low–Density Lipoproteins. Diabetes Vol 31 (1982) 1098–1104.

Arbogast, BW, et al. Plasma Factors that Determine Endothelial Cell Lipid Toxicity in Vitro Correctly Identify Woman with Preeclampsia in Early and Late Pregnancy. Hypertension in Pregnancy Vol 15 (1996) 263–279.

Arbogast, BW, et al. A New Protective Factor in Coronary Artery Disease: Very Low–Density Lipoprotein Toxicity–Preventing Activity. Atherosclerosis Vol 57 (1985) 75–86.

Basu, S.P., et al. Influence Of Fatty Acid and Time of Focusing on the Isoelectric Focusing of Human Plasma Albumin. Biochimica Biophysica Acta Vol 533 (1978) 66–73.

Arbogast, BW. Purification and Identification of Very Low Density Lipoprotein Toxicity Preventing Activity. Atherosclerosis Vol 73 (1988) 259–267.

Vigne Jean–Louis et al: "Elevated non–esterified fatty acid concentrations in severe preeclampsia shift the isoelectric characteristics of plasma albumin." Journal of Clinical Endocrinology & Metabolism, Vol 82, No. 11, No. 1997, pp. 3786–3792.

Endresen M J et al: "Increased lipolytic activity and high ratio of free fatty acids to albumin in sera from women with preeclampsia leads to triglyceride accumulation in cultured endothelial cells". American Journal of Obstretrics and Gynecology, vol. 167, No. 2, 1992, pp. 440–447.

Frayn Dieth N et al: "Are increased plasma non–esterified fatty acid concentrations a risk marker coronary heart disease and other chronic heart diseases?" Clinical Science, vol. 90, 1996, pp. 243–253.

Masue Kazuko et al: "Nonesterified fatty acids (NEFAs) and triglyceride levels are the predictors of blood pressure elevation." Journal of the American College of Cardiology, vol. 33, No. 2 Suppl. A, Feb. 1999, p. 272A—(Abstract).

Egan B M et al: "Vascular effects of non–esterified fatty acids: Implications for the cardiovascular risk factor cluster." Prostaglandins Leukotrienes and Essential Fatty Acids, vol. 60, No. 5–6, May 1999, pp. 411–420.

METHOD FOR THE PREDICTION OF PREECLAMPSIA AND OTHER DISEASES

FIELD OF THE INVENTION

The present invention relates to methods for predicting and following illnesses. More particularly, the present invention relates to the diagnosis of preeclampsia and other diseases.

BACKGROUND OF THE INVENTION

Vascular disease is often related to the composition of blood flowing therethrough. In particular, high concentrations of very low density lipoproteins (VLDL) in blood have a deleterious effect on vascular integrity. Very low density lipoproteins in blood tend to break down the inner vascular walls causing vascular diseases including preeclampsia, atherosclerosis, stroke, peripheral vascular disease, diabetic vascular disease, and such.

Methods providing earlier detection of vascular diseases, and methods for diagnosing a patient's proclivity toward developing a vascular disease at a later point in his life are desirable so that such disease may be better controlled, or even avoided. The early detection of preeclampsia is particularly important.

Preeclampsia is a toxic vascular disease of particular interest. Preeclampsia develops in late pregnancy and is characterized by a sudden rise in blood pressure, excessive increase in weight, generalized edema, albuminuria, severe headaches, and visual disturbances. The blood vessels in a pregnant woman's uterus supplying blood to her placenta and fetus become restricted during preeclampsia, thereby delivering reduced amounts of blood and oxygen to the fetus. Preeclampsia is linked to poor fetal growth and, in its most severe form, can be fatal to both the fetus and the mother.

Human blood's natural defense against the destructive effect of VLDL on Endothelial cells and Leukocytes has been quantified by an index or factor known as the "toxicity preventing activity" or "TxPA" of the blood. (Arbogast, B. W., and Dreher, N. J. *Coronary Disease Prediction Using a New Atherogenic Index. Atherosclerosis*, Vol. 73 (1988) 259–267). (Chi, D. S., et al. *Decreased Lymphocyte Response in Streptozotocin Induced Diabetic Rats: A Function of Very Low Density Lipoproteins. Diabetes* 31 (1982) 1098–1104). U.S. Pat. No. 4,699,878 discloses that the TxPA of a blood sample can be estimated by comparison of the growth of a culture of cells treated with a toxic quantity of VLDL and varying amounts of the blood sample to the "zero" growth of a reference culture of cells which was treated with the same toxic quantity of VLDL and no blood.

The ratio of VLDL to TxPA determines the cytotoxicity of the blood in in vitro cell cultures. The ratio of in vitro VLDL to TxPA has also been effective in determining in vivo vascular injury. The presence of or future development of preeclampsia can be predicted with a 90% accuracy using the ratio of VLDL to TxPA. (Arbogast, B. W., Leeper, S. C., Merrick R. D., Olive, K. E. and Taylor, R. N *Plasma Factors that Determine Endothelial Cell Lipid Toxicity in vitro Correctly Identify Women with Preeclampsia in Early and Late Pregnancy. Hypertension in Pregnancy* Vol. 15 (1996) 263–279). Similar accuracy has been achieved with atherosclerosis. (Arbogast, B. W., Gill, L. R. and Schwertner, H. A. *A New Protective Factor in Coronary Artery Disease: Very-Low-Density Lipoprotein Toxicity-Preventing Activity.* Atherosclerosis Vol. 57 (1985) 75–86). (Arbogast, B. W. and Dreher, N. J. *Coronary Disease Prediction Using a New Atherogenic Index. Atherosclerosis* Vol. 66 (1987) 55–62). The drawbacks of this cell culture method are that it is a relatively expensive assay and that it requires cell growth time. Also, the level of uncertainty is about 10%, undesirably high for a medical assay.

Blood plasma contains components including albumin, non-esterified fatty acids (NEFA), and triglycerides which are carried in varying amounts on very low density lipoproteins (VLDL), low density lipoproteins (LDL), and high density lipoproteins (HDL). Human blood albumin exists as two species that may be separated by their electrophoretic migration to isoelectric points of pH 4.8 and pH 5.6. (Basu, S. P., Rao, S. N. and Hartsuck, J. A. *Influence of Fatty Acid and Time of Focusing on the Isoelectric Focusing of Human Plasma Albumin. Biochim Biophys Acta,* Vol. 533 (1978) 66). It has been found that the toxicity preventing activity of human blood is mainly provided by pI 5.6 albumin. Arbogast disclosed that the pI 5.6 albumin species provides the protective effect against VLDL damage to vasculature endothelial cells and leukocytes. (Arbogast, B. W. *Purification and Identification of Very Low Density Lipoprotein Toxicity Preventing Activity. Atherosclerosis* Vol. 7 (1988) 259–267 and Chi, D. S., Berry, D. L., Dillon, K. A. and Arbogast, B. W.: *Decreased Lymphocyte Response in Streptozotocin Induced Diabetic Rats: A Function of Very Low Density Lipoproteins. Diabetes* 31: 1098–1 104, 1982). Accordingly, the determination of the pI 5.6 albumin concentration in blood would be greatly beneficial in diagnosing vascular and leukocyte associated diseases.

The concentration of pI 5.6 albumin is not determinable from the total albumin concentration, due to the fact that the pI 5.6 and pI 4.8 albumin species exist in human plasma in unpredictable ratios. The TxPA of a sample of plasma can be determined by separating the pI 4.8 albumin from the pI 5.6 albumin via liquid column isoelectric focusing and determining the concentration of the pI 5.6 albumin fraction via absorbance spectrometry. The concentration of pI 5.6 albumin in plasma is then compared to a standard concentration known to indicate delineation between patients having been diagnosed with arterial disease and those not diagnosed with arterial disease. (Arbogast, B. W., Leeper, S. C., Merrick, R. D., Olive, K. E. and Taylor, R. N.: *Plasma Factors that Determine Endothelial Cell Lipid Toxicity in vitro Correctly Identify Women with Preeclampsia in Early and Late Pregnancy. Hypertension in Pregnancy* 15:263–279, 1996). The electrophoretic method disclosed by Arbogast is quite cumbersome and expensive for clinical operation. The degree of uncertainty of the electrophoresis method is about 10%.

In light of the above, it would be desirable to have a simpler process for diagnosing the presence of or the proclivity toward developing albumin-inhibited VLDL-sensitive diseases, including vascular and non-vascular diseases and conditions. A process not requiring cell culture growth or an isoelectric focusing separation would be more useful would be further desirable for such new diagnostic process to be more accurate than previous processes.

SUMMARY OF THE INVENTION

The present invention is a process for determining the toxicity preventing ability of plasma against a disease having a correlation to a reduction in the concentration of pI 5.6 albumin in the plasma. The present process comprises the steps of:

(a) providing a plasma sample containing free albumin, free non-esterified fatty acids, triglycerides, very low density lipoproteins, low density lipoproteins, and high density lipoproteins;

(b) determining the concentration of the free albumin;

(c) determining the concentration of the free non-esterified fatty acids; and (d) calculating a value indicative of the toxicity preventing ability of the plasma by comparing the concentration of the free albumin to the concentration of the free non-esterified fatty acids. The preferred indicator value is a "TxPA-S ratio", calculated by dividing the concentration of the free albumin by the concentration of the free non-esterified fatty acids.

The present invention further includes an assay kit useful for conducting the present process. The assay kit comprises the following:

(a) a lipid-precipitating reagent;

(b) a reagent that displays a color upon binding with albumin; and (c) a reagent that displays a color upon binding with non-esterified fatty acids.

DETAILED DISCLOSURE OF THE INVENTION

Figure 1:
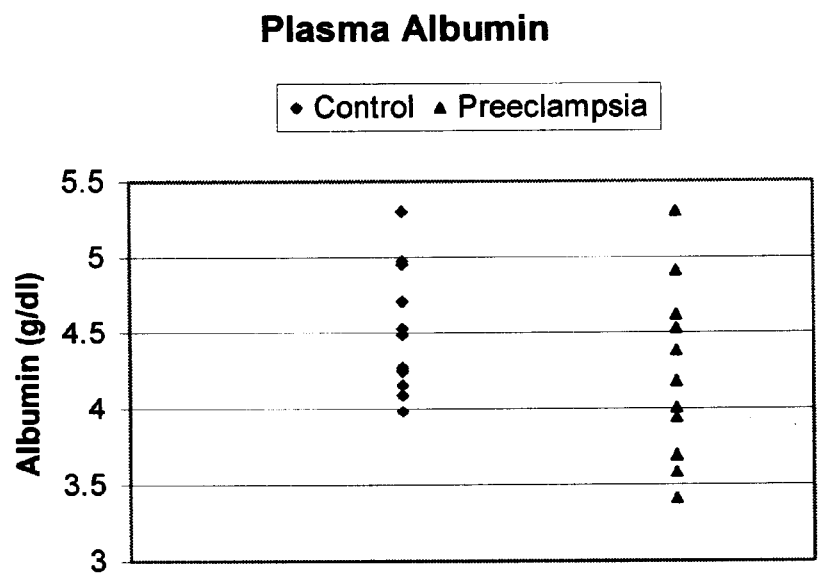
FIG. 1 illustrates a plot showing the lack of diagnostic separation that occurs by comparing the plasma albumin concentration of severe preeclampsia patients and control patients. Control patients are matched with preeclamptic patients on the basis of gestational age, maternal age and race.

The applicant has discovered a new process for predicting the ability of plasma to prohibit deleterious cell injury from blood toxins, particularly against VLDL-cytotoxicity. The process of the present invention is based upon the applicant's discovery that the toxicity inhibiting ability of blood can be indicated by the particular pI 5.6 albumin that is not bound to VLDL. Albumin not bound to VLDL is referred to herein as "free albumin". While the Applicant has found that direct measurement of free pI 5.6 albumin provides an indication of the toxicity inhibiting activity under the present invention, such direct measurement would require separation of the pI 5.6 albumin from the pI 4.8 albumin as well as separating the free albumin from the VLDL-bound albumin. In an effort to find an alternative to a cumbersome electrophoretic focusing assay for separating pI 5.6 albumin from pI 4.8 albumin, the applicant has found that the concentration of free (total) albumin and the concentration of non-esterified fatty acids ("NEFA") bound to free albumin can be compared to provide a very good estimation of the concentration of free pI 5.6 albumin. This provides an easier process since both of these quantities are measurable by simple in vitro techniques. The applicant has found that a ratio of the concentration of free albumin to the concentration of NEFA bound to free albumin (referred to herein as "free NEFA") is an improved indicator of the ability of plasma to prohibit cell injury from blood toxins. However, other diagnostic values calculated largely based on the free albumin and free NEFA concentration are considered to be modifications of the present invention.

It should be noted that the diagnostic ratio determined by the present process is based upon different parameters than the TxPA value previously used to indicate the toxicity inhibiting ability of blood in U.S. Pat. No. 4,699,878 or the isoelectric focusing method used to isolate pI 5.6 albumin. Accordingly, the two values are not comparable. In order to clearly distinguish the new toxicity inhibiting ability diagnostic ratio determined by the present invention from the TxPA value previously used in the art, the diagnostic ratio determined by the present invention is hereinafter referred to as the "TxPA-S ratio", with the "S" indicating that a plasma supernatant is assayed. Determination of the TxPA-S ratio and diagnosis based thereon, according to the present invention, provides an accurate indication of the potential for developing an albumin-inhibited disease using assay methods much simpler than electrophoresis and cell culturing.

The present invention includes a process for determining a TxPA-S ratio for blood and a method of making a medical diagnosis based on the TxPA-S ratio thus determined. The present process can be conducted by testing a sample of blood, serum, or plasma. Since blood is difficult to analyze due to coagulation, serum and plasma processed from whole blood are preferable. The specific type of assays used to conduct the process of the present invention will determine whether serum or plasma would be the most preferable blood form. Although plasma is the most preferred blood form for the present process, the term "plasma" is hereinafter used to indicate blood, serum, and/or plasma.

The most pertinent components of plasma assayed in the present invention are free albumin, NEFA having an acyl chain length of 6 to 20 carbons, triglycerides having an acyl chain length of 6 to 20 carbons, low density lipoproteins ("LDL"), very low density lipoproteins ("VLDL"), and high density lipoproteins ("HDL"). VLDL have a density less than about 1.006 gm/ml. LDL have a density of about 1.006 to about 1.063 gm/ml. HDL have a density greater than about 1.063 gm/ml. The NEFA component is made up of VLDL-bound NEFA and NEFA not bound to VLDL. Since it has been found that the overwhelming majority of NEFA not bound to VLDL is free NEFA, the term "free NEFA" is hereinafter used interchangeably to refer to either type of NEFA entity, unless otherwise specified.

The present process comprises determining the concentration of free albumin (both pI 4.8 and pI 5.6 albumin) and the concentration of free NEFA in a plasma sample and calculating the TxPA-S ratio of the plasma by dividing the concentration of free albumin by the concentration of free NEFA. The concentration of free NEFA is preferably determined after removal of the VLDL from the plasma. The albumin concentration may be measured either as the total plasma albumin before the VLDL is removed or as the free albumin remaining after the removal of VLDL. However, a more accurate TxPA-S ratio is obtained using the free NEFA concentration and the free albumin concentration to calculate the TxPA-S ratio.

It is more preferable that the free albumin and free NEFA concentrations measured do not include albumin or NEFA bound to LDL. Accordingly, it is preferred that the LDL is removed from the plasma along with the VLDL. The TxPA-S ratio has been found to be accurate when the free albumin and free NEFA measured does not include LDL-bound entities.

After determining the TxPA-S ratio, the TxPA-S is preferably used to classify the toxicity preventing ability of the plasma for a particular albumin-inhibited toxic disease or condition by comparing the TxPA-S ratio to a standard TxPA-S for that specific disease. The standard TxPA-S is determined by conducting the process of the present invention on a statistically significant plurality of plasma samples having known potentials for the suspected albumin-inhibited disease or condition. The TxPA-S ratio determined for each of the plasma standards is categorized according to an independent medical diagnosis for the suspected albumin-inhibited disease. A positive diagnosis for the suspect albumin-inhibited disease is typically based on the actual development of the disease within a given period. A negative diagnosis for the albumin-inhibited disease is typically based upon the non-development of the disease over a given period. The standard may be a single benchmark TxPA-S ratio or, preferably, a range of TxPA-S ratios indicative of a high potential for the albumin-inhibited disease. The most preferable standard is a pair of TxPA-S ratio ranges, with one of the ranges representing TxPA-S ratios indicating a high potential for the albumin-inhibited disease and the other range indicating a low potential for the same disease.

The process of the present invention provides an unexpectedly high amount of separation between such a pair of high and low potential TxPA-S ratio standard ranges. The TxPA-S standard ratios obtained from a sufficiently large population of plasma standards, most preferably aggregate into two essentially exclusive ranges, i.e., no overlapping between the two ranges except for a statistically minor number of outliers.

Thus, the accuracy in diagnosis using the present process is higher than previous processes. A sample TxPA-S ratio falling within the higher standard range indicates that the patient has a significantly low potential for developing the suspected disease. A sample TxPA-S ratio falling within the lower standard range indicates that the patient has a significantly high potential for developing the disease. A test TxPA-S ratio falling between the two standard ranges would be indeterminate of the risk of development of the disease.

An even more accurate determination of a patient's proclivity toward developing an albumin-inhibited disease is made when the present process further comprises the step of measuring the total triglyceride concentration in the plasma and incorporating the triglyceride concentration into the diagnostic equation. The triglyceride concentration may be taken into consideration in determining the patient's disease potential by evaluating a plot of TxPA-S ratio versus triglyceride concentration. From such a plot, a linear equation separating the high disease potential plasma from the low disease potential plasma can be calculated. Diagnosis of a plasma sample can be easily made by entering both the TxPA-S ratio and the triglyceride concentration into the equation. The high and low disease-potential standard ranges are further narrowed and separated from each other when the triglyceride concentration effect is included in the diagnosis. However, the stark improvement in diagnosis accuracy using TxPA-S ratios instead of TxPA values is further evidenced by the fact that the triglyceride concentration has significantly less of an effect on the amount of separation between diagnosis standard ranges based on TxPA-S ratios, compared to its effect on TxPA value standard ranges.

The diseases that may be diagnosed by the present process are diseases having a correlation to a reduction in the concentration of pI 5.6 albumin in the plasma. The process is especially useful in predicting vascular diseases caused by the breakdown of endothelial cells due to VLDL attack. The term "disease" is used herein to refer to diseases and other medically diagnosable conditions. Examples of such diseases are preeclampsia, atherosclerosis, stroke, nephrotic syndrome (kidney disease), peripheral vascular disease, and diabetic vascular disease. Examples of non-vascular diseases and conditions not recognized as vascular diseases but which have a correlation to the albumin concentration are cancer, mortality, morbidity, sepsis, shock and aging.

The particular methods used to remove the VLDL, measure free NEFA, and measure albumin are not critical. Various methods for conducting each step in the present process are known in the art. Examples of suitable methods and reagents are provided below, but should not be construed to be limiting on the scope of the present invention.

Even though the NEFA concentration of interest is the NEFA bound to free albumin, a determination of non-VLDL bound NEFA concentration has been found to be a useful approximation of the NEFA bound to free albumin, for the present process. Thus, any technique that provides differentiation between the VLDL-bound NEFA and the non-VLDL bound NEFA is suitable for determining the concentration of free NEFA. The VLDL-bound NEFA can be distinguished from the free NEFA after removing the VLDL from the plasma.

The VLDL may be removed from the plasma sample by a number of techniques. Examples of such separation means include any known techniques for removing LDL and/or VLDL including ultacentrifugation, precipitation by sulfated glycans or phosphotungstic acid in the presence of divalent cations, immuno-precipitation, electrophoresis, isoelectric focusing, charge separation techniques such as ion exchange chromatography, size separation techniques such as gel filtration chromatography, and the like. The VLDL is most preferably removed from the plasma sample by way of precipitation, followed by filtration, siphoning or decantation of the supernatant from the precipitated solids.

The VLDL may be precipitated by use of a non-albumin binding lipid precipitating reagent. A preferred reagent includes a sulfated glycan such as dextran sulfate, and a divalent cation such as magnesium chloride. An example of a commercially available precipitating reagent useful for precipitating VLDL is the HDL-Cholesterol Precipitating Reagent comprised of dextran sulfate, magnesium chloride, sodium chloride, and polyethylene glycol, available commercially from RefLab Medical Analysis Systems, Inc. This preferred precipitating reagent is a mixture of dextran sulfate (0.2 mM), magnesium chloride (63.9 mM), sodium chloride (63.3 mM), and polyethylene glycol (3.3 mM). It is preferable to remove LDL from the plasma sample along with VLDL. LDL typically precipitates out of solution along with VLDL. The precipitated VLDL and LDL solids may be removed by known methods such as by centrifugation of the solution followed by decantation of the plasma supernatant. An alternative VLDL and LDL precipitation reagent is composed of 30.3 mM phosphotungstic acid and 100 mM magnesium chloride. This solution is mixed in a 1:5 sample to reagent ratio and the precipitated VLDL and LDL solids removed as stated above for the dextran-magnesium precipitation.

After removing the VLDL, the free NEFA concentration may be determined from the supernatant by any method known to determine fatty acid concentration. Examples of such methods are disclosed in U.S. Pat. Nos. 4,071,413; 4,360,591; 4,349,625; 4,301,244; and 4,229,538. Suitable methods of measuring NEFA concentration include titration, colorimetry, and radioisotope methods, with colorimetry being preferred. Appropriate solvent systems for extracting NEFA are disclosed by Dole, V. P. *J. Clin. Invest* Vol 35 (1956) 150. Extracted NEFA may be measured by titration with standard alkali to an acid-base indicator endpoint.

Radiochemical methods for determining NEFA concentration involve extracting the NEFA into the heptane phase of a Dove extract and freeing it of phospholipids. The extract is then labeled with radioactive $^{63}Ni$ by mixing it with radioactive nickel nitrate. The upper, organic phase containing the nickel-fatty acid complex is thereafter assayed for radioactivity. $^{60}Co$ can replace $^{63}Ni$, but is more hazardous because it is a gamma emitter.

Various methods of colorimetric determination of NEFA concentration are known in the art and may be conducted on NEFA extracted from the supernatant or on the NEFA as it exists in vitro in the supernatant. Extraction methods are typically based on the formation of copper or cobalt salts and the extraction of the salt into a non-polar organic solvent where it is complexed with a chromogen dye for calorimetric measurement. Alternatively, and more preferably, the NEFA may be measured in vitro using an enzymatic colorimetric method. One such method involves treating the supernatant with acyl Coenzyme A synthetase in the presence of added adenosine triphosphate (ATP), magnesium cations and CoA, to form the thiol esters of CoA known as Acyl CoA as well as the by products adenosine monophosphate (AMP) and pyrophosphate (PPi). The Acyl CoA thereby produced is then oxidized with Acyl CoA Oxidase, with the generation of hydrogen peroxide. Hydrogen peroxide, in the presence of peroxidase, permits the oxidative condensation of 3-methyl-N-ethyl-N-β-hydroxyethyl-aniline with 4-aminoantipyrine thus forming a purple-colored adduct. The concentration of NEFA in the supernatant may be determined from the optical density measured at a maximum absorbance of 550 nm.

It has been found that ascorbic acid (Vitamin C) existing in plasma often causes significant interference in the determination of NEFA concentration when using this calorimetric assay. This is largely due to the biological role of ascorbic acid as an antioxidant and it's ability to react with hydrogen peroxide. Therefore, when using this type of a calorimetric method to determine NEFA concentration, it is preferable to remove ascorbic acid from the plasma or the plasma supernatant prior to calorimetric determination of NEFA concentration. The addition of ascorbate oxidase (AOD) is a convenient way of removing ascorbic acid.

In the step of determining the albumin concentration, it is preferable that the albumin concentration determined is the concentration of free albumin. Accordingly, the albumin concentration is preferably measured from the plasma supernatant remaining after removal of VLDL more preferably after removed of both VLDL and LDL. Albumin concentration may be measured by known methods such as an enzyme linked immunoabsorbent assay (ELISA), immunoassay, radioimmunoassay (RIA), dye binding calorimetric analysis, and through measuring the amount of protein or amino acid after purification of the albumin using precipitation, electrophoresis, electrofocusing, gel filtration, ion exchange chromatography, affinity chromatography and such. A dye binding colorimetric assay is the preferred assay methodology for determining albumin concentration since it is simpler and less time consuming than other procedures. In general, when a dye binds to a site on the albumin molecule it becomes detectable due to the difference in the pH environment on the albumin mass and in the solution. Examples of such calorimetric dye binding albumin assays are disclosed in U.S. Pat. Nos. 5,182,214; 4,568,647; 3,873,272; 3,884,637; 5,194,390; 4,337,064; and 4,230,456. A preferred colorimetric assay for determining albumin concentration includes mixing about 1 to about 10 $\mu L$ of supernatant or plasma with about 50 to about 200 $\mu L$ of a 0.030 mmol/liter bromcresol green (pH 4.2) albumin reagent. The albumin concentration may be determined by measuring optical density at a maximum absorbance of 628 nm.

An alternative means of determining a value indicative of the free pI 5.6 albumin concentration comprises measuring the concentrations of albumin and NEFA bound to VLDL and subtracting those concentrations from the total concentrations of albumin and NEFA in serum, thereby obtaining a concentration of free albumin and a concentration of free NEFA. These concentrations could thus be used to calculate a TxPA-S value as provided above.

The TxPA-S ratio for a given sample of plasma is calculated according to the present invention by dividing the concentration of free albumin by the concentration of free NEFA. The concentration units used are not important, as long as the same units are used to obtain the TxPA-S ratio standard. For example, the TxPA-S value may be expressed as mg albumin/mg NEFA or absorbance albumin/absorbance NEFA or as a combination of the above units.

It should be understood that, although the preferred embodiment of the process which includes the determination of the TxPA-S ratio is described above, the present invention also includes a process wherein the actual concentration of the free pI 5.6 albumin, or else any other indicator of such, is determined and used as the value indicative of the toxicity preventing ability of blood for the particular disease. Such an embodiment of the present invention comprises the steps of providing a plasma sample as described above, determining an indication of the concentration of free pI 5.6 albumin in the plasma, and evaluating the toxicity preventing ability of the plasma against the disease by comparing the concentration of the free pI 5.6 albumin to a standard obtained by conducting each of said steps (a) and (b) on a plurality of plasma samples, with each of the plurality of plasma samples being withdrawn from a patient having a known diagnosis for the presence of or the development of said disease. One skilled in the art would realize that the direct measurement of the concentration of free pI 5.6 albumin would not be as economically feasible as the measurement of free albumin and free NEFA due to the complexity of conducting electrophoretic focusing to separate the pI 5.6 albumin from the pI 4.8 albumin.

The preferred process of the present invention includes measuring the triglyceride concentration and factoring the level found into the diagnosis. The triglyceride concentration may be determined by conducting an enzymatic colorimetric endpoint assay.

The present invention further includes an assay kit which is a particular combination of reagents useful for conducting the preferred process of the present invention wherein VLDL are removed via precipitation prior to determining the concentration of NEFA and albumin remaining in the supernatant determined via calorimetric assays. The assay kit of the present invention includes a VLDL precipitating reagent, an albumin binding pH-sensitive dye, and an enzymatic fatty acid, a colorimetric reagent. The assay kit of the present invention preferably includes an ascorbic acid oxidizing agent such as ascorbate oxidase.

The assay kit also preferably includes a triglyceride enzymatic colorimetric endpoint reagent. A calorimetric reagent suitable for binding with and indicating triglyceride includes a compound and enzyme that work together to hydrolyze triglycerides to glycerol and fatty acids. Adenosine tri-phosphate (ATP) and glycerol are reacted with glycerokinase to form glycerol-1-phosphate and adenosine di-phosphate. Glycerol-1-phosphate (G-1-P) can be oxidized to produce hydrogen peroxide, which is measured similarly to the NEFA reagent. Alternatively, G-1-P can react with nicotine adenine di-nucleotide (AND) to produce reduced nicotine adenine di-nucleotide (NADH). NADH then reduces a dye that changes color upon reduction forming formazan. Or in the preceding assay pyruvate can be added to NADH in the presence of lactate dehydrogensase and the resulting NAD can be determined using ultraviolet light. In an alternative method triglycerides are hydrolyzed with alcoholic KOH to form glycerol and free fatty acids. Glycerol and ATP then react in the presence of glycerokinase to form glycerol-1-phosphate and ADP. In the next step ADP combines with phosphoenol pyruvate in the presence of pyruvate kinase to form pyruvate and ATP. Pyruvate then reacts with NADH in the presence of lactic dehydrogenase to form lactate and NAD. NAD is then measured with ultraviolet light.

The VLDL precipitating reagent of the present diagnostic test kit preferably includes either dextran sulfate as the sulfated glycan and magnesium chloride as the divalent cation or phosphotungstic acid and magnesium chloride.

The pH-sensitive albumin binding dye is preferably selected from the group of dyes consisting of bromcresol green, bromcresol purple and the like. The preferred enzymatic fatty acid calorimetric reagent is a mixture including acyl coenzyme A synthetase, adenosine triphosphate, and coenzyme A. In regard to the various reagents in the kit of the present invention, a compound is herein considered to have displayed a color upon binding with a plasma entity when a color is displayed at any time due to a chemical reaction occurring on the plasma entity as a result of contacting the reagent with the plasma.

This invention can be further illustrated by the following examples, illustrating preferred embodiments thereof. However, it should be understood that these examples are included merely for purposes of illustration and are not intended to limit the scope of the invention unless otherwise specifically indicated.

EXAMPLES

In the following examples, blood samples were drawn from pregnant women who did not have preeclampsia at that time. The development of preeclampsia or lack of development of preeclampsia in these patients was confirmed at the end of the pregnancies. Examples 1–6 involve blood samples drawn from women who later developed severe preeclampsia, defined as women who had late-pregnancy hypertension (an absolute blood pressure of at least 140/90 torr or a rise of at least 30 torr systolic or at least 15 torr diastolic over values in the first 20 weeks), proteinuria (at least 30 mg protein/dL urine in a catheterized specimen or at least 60 mg/dL in voided urine), and hyperuricemia (serum uric acid>1 standard deviation above normal for gestational age) and did not carry to term. Examples 7–9 involve blood samples drawn from women who later developed mild preeclampsia, defined as having the same criteria as defined for severe preeclampsia, except they were able to carry their pregnancies to term.

The following reagents were used in the examples:

Precipitating Reagent—
RefLab brand HDL-cholesterol precipitating reagent, available from Medical Analysis Systems, Inc, (USA), containing 0.2 mM dextran sulfate, 63.9 mM magnesium chloride, 63.3 mM sodium chloride, and 3.3 mM polyethylene glycol.

Albumin Binding Reagent—
Albumin assay kit available from Wako chemicals USA, Inc, contains a 0.2 mmole/L solution at pH 3.8 of bromcresol green in 50 mmole/L citrate buffer.

NEFA Binding Reagent With Ascorbic Acid Remover—
assay kit available from Wako Chemicals USA, Inc, Richmond, Va. Reagent A was prepared for the purpose of oxidizing ascorbic acid and acetylating Co enzyme A for determination of NEFA. Reagent B was prepared for the purpose of oxidizing acyl CoA and generating hydrogen peroxide for determination of NEFA. The hydrogen peroxide then reacts with 3-methyl-N-enthyl-N-β-hydroxyethyl-aniline and 4-aminoantipyrine to form a purple color.

| Reagent A: | |
|---|---|
| ACS (Acyl Coenzyme A Synthetase) | 3 U/vial |
| AOD (Ascorbate Oxidase) | 15 U/vial |
| CoA (Coenzyme A) | 7 mg/vial |
| ATP (Adenosine Triphosphate) | 30 mg/vial |
| 4-Aminoantipyrine | 3 mg/vial |

A 10 ml diluent (0.05 M phosphate buffer, pH 6.9, 3 mM magnesium chloride, surfactant and stabilizers) was added to each vial of reagent A to make working Solution A.

| Reagent B: | |
|---|---|
| ACOD (Acyl Coenzyme A Oxidase) | 132 U/vial |
| POD (peroxidase) | 150 U/vial |
| MEHA (3-methyl-N-ethyl-N-β-hydroxyethyl-aniline) | 4 mg/vial |

Working Solution B was prepared by diluting reagent B with 20 ml of phenoxyethanol (0.3% v/v) and a surfactant.

Example 1 (Comparison)

FIG. 1 illustrates the lack of diagnostic separation that occurred by simply measuring the total albumin concentration in plasma from 11 preeclamptic women and 11 matched controls.

Example 2 (Comparison)

The same process of measuring (total) albumin was conducted as in Example 1 on the same plasma samples, except that the VLDL was removed from the plasma prior to measuring the albumin concentration. The VLDL was precipitated from each plasma sample by combining 100 μL of the plasma and 100 μL of precipitating reagent in a centrifuge tube (either the 1:1 or 1:5 sample to reagent ratio is acceptable depending on the concentration of the reagent). The centrifuge tube was shaken on a vortex mixer to obtain thorough mixing and then centrifuged for 10 minutes at 3,000 rpm. The supernatant was decanted by pipetting into a clean test tube. The albumin concentration was determined using the resultant supernatant. The results are shown in FIG. 2.

Figure 2:
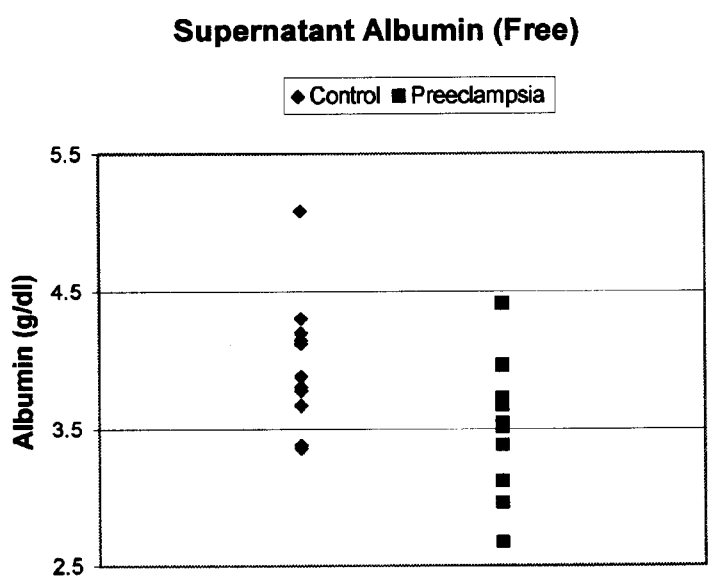
FIG. 2 illustrates a plot similar to FIG. 1 except that the albumin concentration is the albumin found in the plasma supernatant after removing VLDL and LDL by precipitation and centrifugation.

Comparison of the data shown in FIGS. 1 and 2 show that there is some improvement in separation of albumin concentration between the group of preeclamptic blood samples and the control blood samples when the VLDL component is removed prior to measuring albumin. There is less overlap in FIG. 2 than in FIG. 1. The mean albumin concentration for the control, patient blood samples is higher than the mean albumin concentration for the preeclamptic patient blood samples.

Example 3 (Comparison)

This example illustrates the separation of NEFA concentration between the 11 preeclamptic and 11 control patient blood samples of example 1. The plasma processed from the blood samples was tested for NEFA concentration (no removal of VLDL). To measure the NEFA concentration, five μL of plasma was pipetted into the well of a flat-bottomed microtiter plate. The working solution for reagent A was added, (70 μL) the solution mixed well and the plate incubated at 37° C. for 10 minutes. The working solution for reagent B was then added (140 μL), the plate mixed well and incubated at 37° C. for another 10 minutes. The optical density was measured at a wavelength of 550 nm on a microtiter plate reader. The absorbance from a water blank was subtracted and the concentration of NEFA was recorded as a proportion to the resulting absorbance as compared to a known standard.

Figure 3:
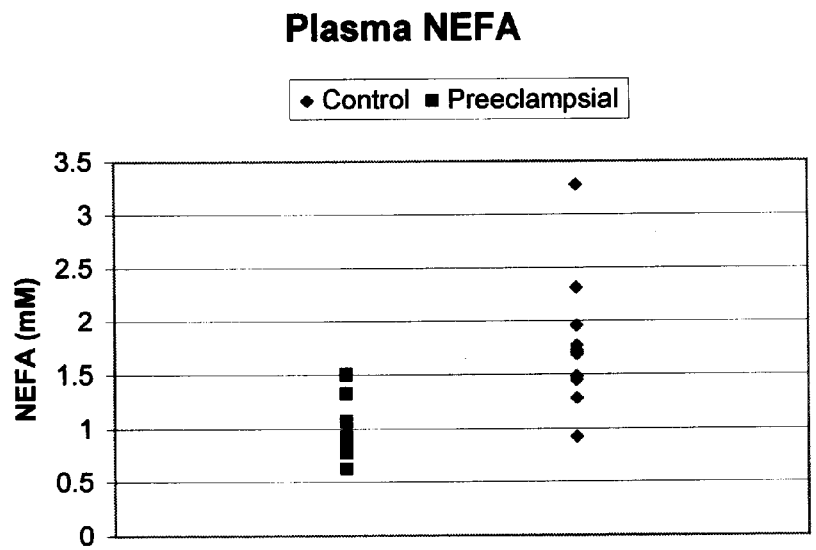
FIG. 3 illustrates a plot showing that some diagnostic separation occurs by comparing the plasma NEFA concentration of severe preeclampsia patients and control patients.

The results are graphically shown in FIG. 3.

Example 4

Example 4 illustrates the methods used to conduct the process of the present invention.

The 22 plasma samples were tested as in example 3, except that the VLDL was removed from the plasma to provide a bound albumin free supernatant prior to measuring NEFA concentration. The VLDL was precipitated from the plasma sample by combining 100 μL of the plasma and 100 μL of the precipitating reagent in a centrifuge tube. The centrifuge tube was shaken on a vortex mixer to obtain thorough mixing and then centrifuged for 10 minutes at 3,000 rpm. The supernatant was decanted by pipetting into a clean test tube. The NEFA concentration of the supernatant was measured according to the method used in example 3. The results are shown in FIG. 4.

Figure 4:
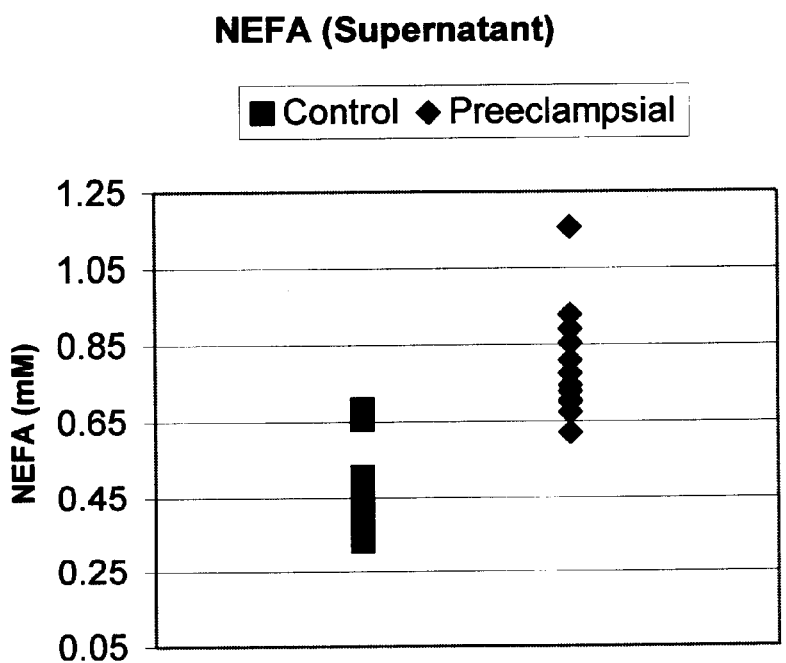
FIG. 4 illustrates a plot similar to FIG. 3 except that the NEFA concentration is the NEFA found in the plasma supernatant after precipitation of VLDL and LDL.

Comparison of the FIG. 3 to FIG. 4 illustrates that the concentration of NEFA in the patient samples is significantly separated between the preeclamptic samples and the control samples when the VLDL is first removed from the plasma. This indicates that a significant amount of the NEFA in plasma is bound to VLDL, in addition to being bound to albumin. Therefore, the removal of VLDL-bound NEFA and VLDL-bound albumin allows for a more precise measurement of the concentration of NEFA bound to free albumin, which strongly correlates with the toxicity preventing ability of the blood.

Example 5

Albumin to NEFA ratios were calculated for each of the 22 patient samples using the result of Examples 1–4. The ratio was first calculated by dividing the albumin concentration determined in example 1 (plasma sample) by the NEFA concentration determined in Example 3 (plasma sample). These results are plotted in FIG. 5.

TxPA-S ratios were calculated according to the present invention for each of the 22 patient samples by dividing the albumin concentration determined in Example 2 (supernatant measured) by the NEFA concentration determined in Example 4 (supernatant measured). These results are plotted in FIG. 6.

Figure 5:
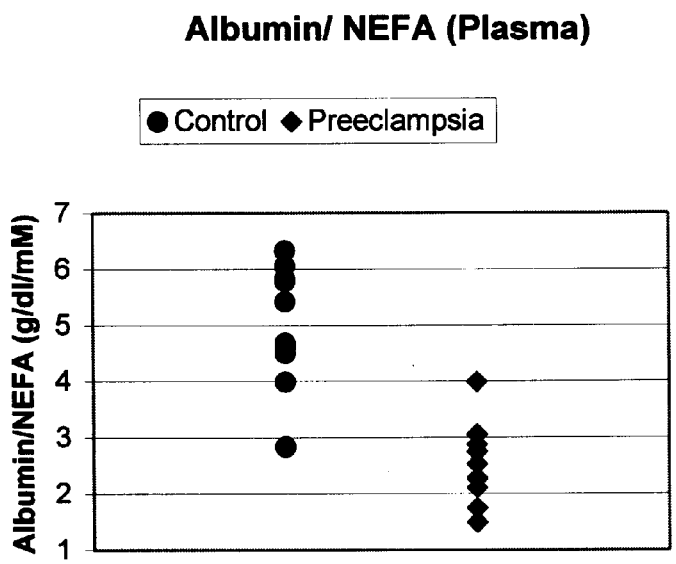
FIG. 5 illustrates a graph showing improved diagnostic separation between preeclampsia patients and control patients when a ratio of plasma albumin concentration to plasma NEFA concentration is plotted.
Figure 6:
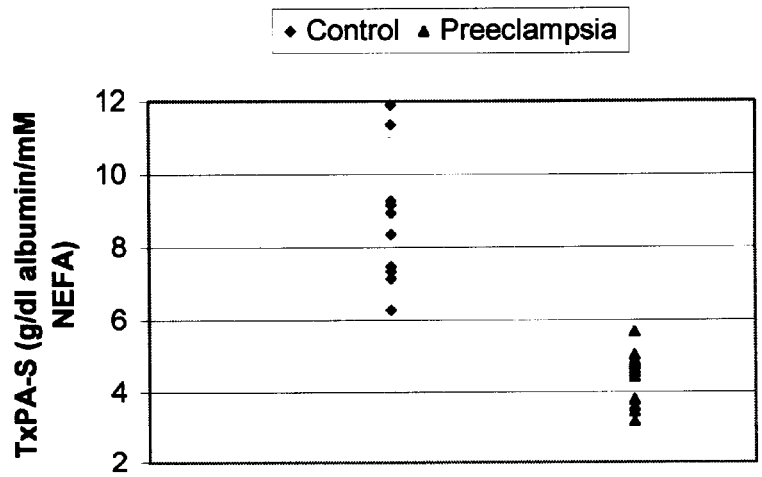
FIG. 6 illustrates a graph showing further improved diagnostic separation between severe preeclampsia patients and control patients when a ratio of supernatant albumin concentration to supernatant NEFA concentration (TxPA-S ratio) is plotted.

Comparison of FIGS. 5 and 6 illustrates the significant amount of separation gained by measuring both the albumin concentration and NEFA in the present process only after the VLDL has been removed. FIG. 6 shows a complete separation between the preeclampsia samples and the control samples.

Analysis of the results shown in FIG. 6 indicated that a TxPA-S ratio falling between about 1.17 and about 1.78 would indicate a normal risk of preeclampsia, with. an approximately 100% degree of certainty. A TxPA-S ratio falling between about 0.63 and about 0.9 would indicate a high risk of preeclampsia, with an approximately 100% degree of certainty. TxPA-S ratios falling between these two ranges would be indeterminate.

The plot shown in FIG. 6 is an example of a TxPA-S ratio standard useful in diagnosis using the present process. For example, a single TxPA-S ratio cut-off value of 1.0 could be used to separate test TxPA-S ratios for diagnostic purposes, if desired. But the use of discreet ranges is more precise, especially with a larger population of reference samples to derive the TxPA-S standard ranges.

Example 6

The present example illustrates a previously used method of determining column TxPA and compares the results with TxPA-S. The (total) albumin concentration of plasma samples obtained from 11 pregnant female patients diagnosed for severe preeclampsia and 11 pregnant female patients matched for gestational age, maternal age and race was measured directly from an aliquot (10:1) of the plasma (no removal of VLDL) by isoelectric focusing, according to the method disclosed by Arbogast in Hypertension in Pregnancy Vol. 15. Ten microliters of plasma is placed in a 10 ml sucrose density (5%–50%) gradient with 0.25 ml ampholine of pI 4–6.5. Current was applied for 18 hours and the column eluted into microtiter plates. One drop fractions were collected. Two hundred microliters of the albumin reagent is mixed with the eluted sample and the color measured at about 660 nm.

Figure 7:
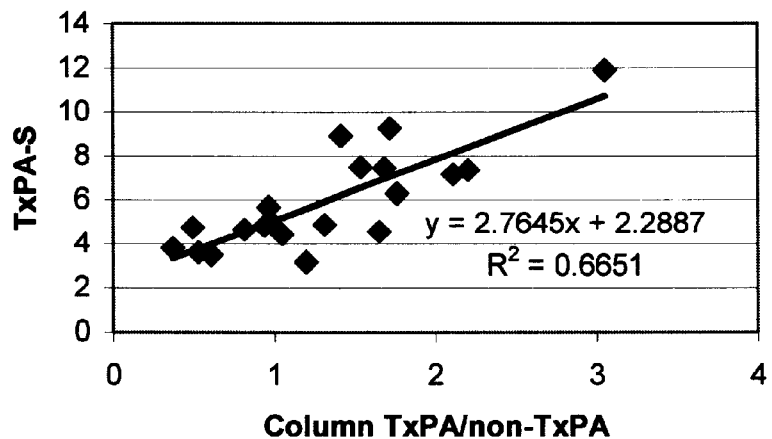
FIG. 7 illustrates a linear correlation plot between the TxPA-S ratios (supernatant) and the column TxPA values (from plasma) measured on the same set of blood samples.

The plot shown in FIG. 7 illustrates the high correlation between the results shown in FIG. 6 for the colorimetric determination of TxPA-S on supernatant aliquots according to the present invention versus the column method determination of TxPA on plasma aliquots from the same patient samples according to the method disclosed by Arbogast in *Hypertension in Pregnancy* Vol. 15. The correlation coefficient ($R^2$) found between the two sets of results was 0.66. The variation of replicates is approximately 10% with the column TxPA method, whereas the present calorimetric method using supernatant has approximately a 2% variation.

Examples 7–9 illustrate use of the present process in women later diagnosed to have mild preeclampsia.

Example 7 (Comparison)

Figure 8:
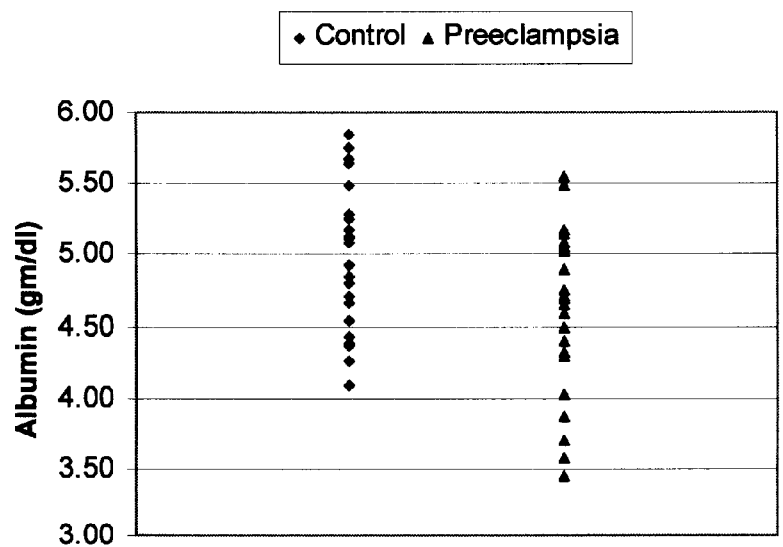
FIG. 8 illustrates a plot similar to FIG. 1, for blood samples taken from a different set of women having mild preeclampsia and a set of control women.

FIG. 8 shows total serum albumin levels in 25 preeclamptic and 25 control women in the third trimester of pregnancy obtained by conducting the same method used in Example 1. As can be seen, a number of the preeclamptic women have total albumin levels (<4 g/dl) below the standard range of the controls. There is, however, significant overlap between the groups which makes total serum albumin levels unsatisfactory for predicting preeclampsia.

Example 8

Figure 9:
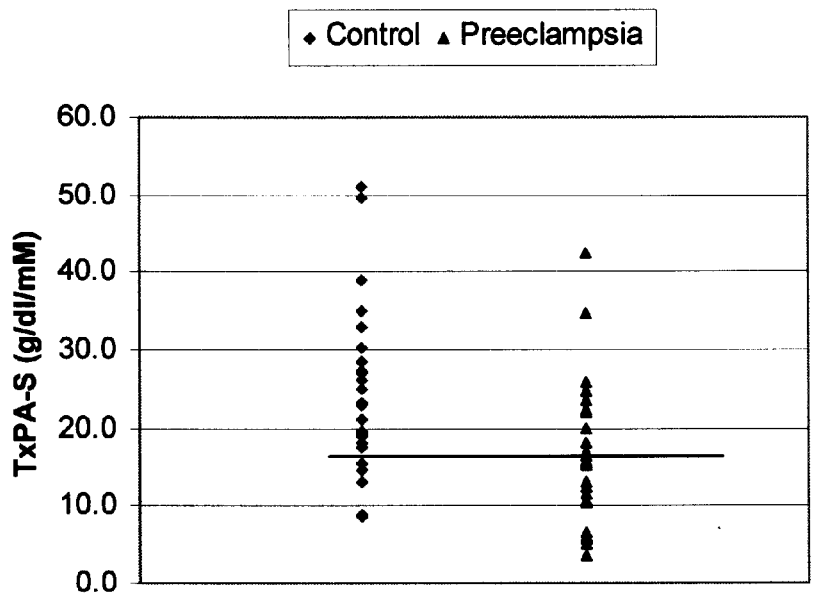
FIG. 9 illustrates a plot similar to FIG. 6, for blood samples taken from the same group of blood samples used in FIG. 8.

The TxPA-S ratio of the same 50 blood samples assayed in Example 7 were determined via the same procedure used in Example 5. FIG. 9 shows that the TxPA-S determined for these same two groups of women resulted in a better separation of the groups than did the measurement of total serum albumin levels in Example 7. Using the horizontal line shown in FIG. 9 as a diagnostic benchmark, 76% (19 of 25) of the controls can be separated from 68% (17 of 25) of the preeclamptics. This is a marked improvement over Example 7.

Example 9

In the present Example, the TxPA-S data determined in Example 8 was further evaluated by multiplying each TxPA-S ratio by the concentration of HDL in the supernatant (after removal of VLDL and LDL). The HDL cholesterol concentration was measured on the supernatant after precipitation of VLDL and LDL using phosphotungstate acid, as disclosed in Lopes-Virella M F, Stone P, Ellis S, Colwell J A. *Cholesterol Determination in High Density Lipoproteins Separated by Three Different Methods. Clin Chem* 23:882–6 (1977), and Allain C A, Poon L S, Chan C S G, Richmond W. Fu P C. *Enzymatic Determination of Total Serum Cholesterol. Clin Chem* 20:470–5 (1974), incorporated herein.

Figure 10:
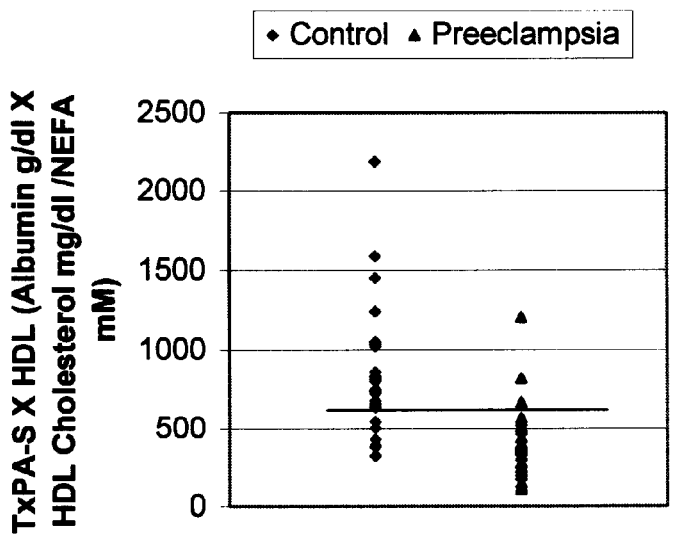
FIG. 10 illustrates a plot similar to FIG. 9, except that a quotient of TxPA-S ratio multiplied by the HDL concentration was plotted instead of TxPA-S alone. This set of blood samples was from a group of women who were outside of the United States. The observation that HDL has a significant contribution to the classification of these women can be either a function of the area of the world where the samples were collected or it may be an integral part of the new methodology for measuring TxPA-S.

FIG. 10 shows the further improvement gained by incorporating the level of HDL into the equation. In this instance 76% (19 of 25) of the Control women are separated from 88% (22 of 25) of the Preeclamptic women.

Although the present invention has been described in terms of the presently preferred embodiment in the specification and in the examples, it is to be understood that such disclosure is not to be interpreted as limiting to the invention described herein. No doubt that after reading the disclosure, various alterations and modifications will become apparent to those skilled in the art to which the invention pertains. It is intended that the appended claims be interpreted as covering all such alterations and modifications as fall within the spirit and scope of the invention.

What is claimed is:

1. A process for determining the toxicity preventing ability of plasma against a disease having a correlation to a reduction in the concentration of pI 5.6 albumin in the plasma, said process comprising the steps of:
   (a) providing a plasma sample containing free albumin, free non-esterified fatty acids having an acyl chain length of 6 to 20 carbons, triglycerides having acyl chain lengths of 6 to 20 carbons, very low density lipoproteins, low density lipoproteins, and high density lipoproteins;
   (b) determining the concentration of the free albumin;
   (c) determining the concentration of the free non-esterified fatty acids; and
   (d) calculating a value indicative of the toxicity preventing ability of the plasma by comparing the concentration of the free albumin to the concentration of the free non-esterified fatty acids, wherein said determining steps (b) and (c) are conducted using a non-cell culture assay.

2. The process according to claim 1 wherein said calculating step comprises dividing the concentration of the free albumin by the concentration of the free non-esterified fatty acids, whereby providing a TxPA-S ratio as the indicative value.

3. The process of claim 1 wherein said step of determining the concentration of the free albumin and said step of determining the concentration of the free non-esterified fatty acids are conducted after a step of removing the very low density lipoproteins from the plasma sample.

4. The process according to claim 1 further comprising a step of determining the concentration of the triglycerides and HDL, further wherein said calculating step (d) includes factoring the concentration of the triglycerides and HDL into the calculation of the value.

5. The process-according to claim 1 or 4 further comprising a step (e) of evaluating the toxicity preventing ability of the plasma against said disease including comparing the value calculated in said step (d) to a standard determined by conducting each of said steps on a plurality of plasma samples, with each of the plurality of plasma samples being withdrawn from a patient having a known diagnosis for the presence of or the development of said disease.

6. The process according to claim 2 further comprising diagnosing the toxicity preventing ability of said plasma by comparing diagnostic factors including said TxPA-S value to a standard determined by conducting the process of claim 2 on a plurality of plasma samples having a known toxicity preventing ability for an albumin inhibited disease.

7. The process according to claim 6 wherein said standard is a single value, a single range of values, or a plurality of ranges of values.

8. The process according to claim 7 wherein said plurality of ranges are essentially exclusive of each other.

9. The process according to claim 1 wherein said disease is preeclampsia, atherosclerosis, stroke, peripheral vascular disease, diabetic vascular disease, nephrotic syndrome, sepsis, shock, cancer, aging, mortality, or morbidity.

10. The process according to claim 3 wherein said step of removing the very low density lipoproteins is conducted by way of precipitation, said step (b) is conducted by performing a colorimetric dye binding assay, ELISA, or a radioimmunoassay, said step (c) is conducted by performing a titration assay, a radioisotope assay or a calorimetric assay including an enzymatic calorimetric assay.

11. The process according to claim 1 wherein said plasma sample contains ascorbic acid and said step of determining the concentration of the free non-esterified fatty acids is conducted after a step of removing the ascorbic acid from said plasma sample.

12. A process for determining the toxicity preventing ability of plasma against a disease having a correlation to a reduction in the concentration of pI 5.6 albumin in the plasma, said process comprising the steps of:

(a) providing a plasma sample comprising a concentration of total free albumin including a concentration of free pI 5.6 albumin and a concentration of free pI 4.8 albumin, triglycerides having acyl chains having from 6 to 20 carbons, very low density lipoproteins, low density lipoproteins, high density lipoproteins, and non-esterified fatty acids bound to the total free albumin, said non-esterified fatty acids having an acyl chain length of 6 to 20 carbons;

(b) determining a value indicative of the concentration of the free pI 5.6 albumin; and (c) evaluating the toxicity preventing ability of the plasma against said disease by comparing the value to a standard value obtained by conducting each of said steps (a) and (b) on a plurality of plasma samples, with each of the plurality of plasma samples being withdrawn from a patient having a known diagnosis for the disease.

13. The process according to claim 12 wherein said determining step (b) is conducted by determining the concentration of the total free albumin and determining the concentration of the non-esterified fatty acids bound to the total free albumin, and calculating the value by comparing the concentration of the total free albumin to the concentration of the non-esterified fatty acids bound to the total free albumin.

14. The process according to claim 12 wherein the value determined in said step (b) is the concentration of the free pI 5.6 albumin in the plasma, wherein said step (b) comprises removing the VLDL and the pI 4.8 albumin from the plasma to provide a plasma supernatant, and thereafter measuring the concentration of the albumin remaining in the supernatant.

15. The process according to claim 12 wherein said disease is preeclampsia, atherosclerosis, stroke, peripheral vascular disease, diabetic vascular disease, nephrotic syndrome, sepsis, shock, cancer, aging, mortality, or morbidity.

* * * * *